(12) United States Patent
Silvestrini

(10) Patent No.: US 8,444,589 B2
(45) Date of Patent: May 21, 2013

(54) OCULAR IMPLANT WITH FLUID OUTFLOW PATHWAYS HAVING MICROPOROUS MEMBRANES

(75) Inventor: Thomas A. Silvestrini, Alamo, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

(21) Appl. No.: 13/157,221

(22) Filed: Jun. 9, 2011

(65) Prior Publication Data

US 2012/0035525 A1 Feb. 9, 2012

Related U.S. Application Data

(60) Provisional application No. 61/353,147, filed on Jun. 9, 2010.

(51) Int. Cl.
*A61B 19/00* (2006.01)

(52) U.S. Cl.
USPC .................................. 604/8; 604/9

(58) Field of Classification Search
None
See application file for complete search history.

(56) References Cited

U.S. PATENT DOCUMENTS

| 5,180,362 | A | 1/1993 | Worst |
| 7,458,953 | B2 * | 12/2008 | Peyman ............ 604/9 |
| 2006/0276739 | A1 * | 12/2006 | Brown ............... 604/8 |
| 2009/0182421 | A1 | 7/2009 | Silvestrini et al. |

* cited by examiner

*Primary Examiner* — Leslie Deak
*Assistant Examiner* — Sara Sass
(74) *Attorney, Agent, or Firm* — Fred C. Hernandez; Mintz Levin Cohn Ferris Glovsky and Popeo, P.C.

(57) ABSTRACT

Disclosed are devices, methods and systems for treatment of eye disease such as glaucoma. Implants are described herein that enhance aqueous flow through the normal outflow system of the eye with minimal to no complications. The implant can include reversibly deformable portions that have a plurality of openings layered, covered or otherwise spanned by an elastomeric film or membrane having micropores. The micropores allow for fluid flow out of the implant while inhibit cellular infiltration and blockage of the openings.

13 Claims, 10 Drawing Sheets

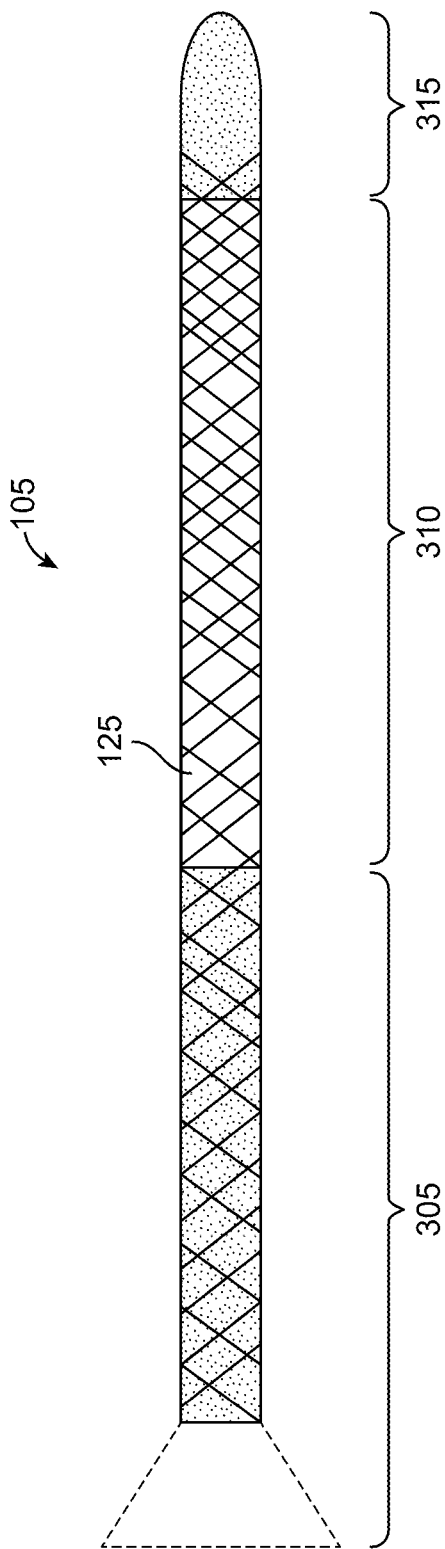
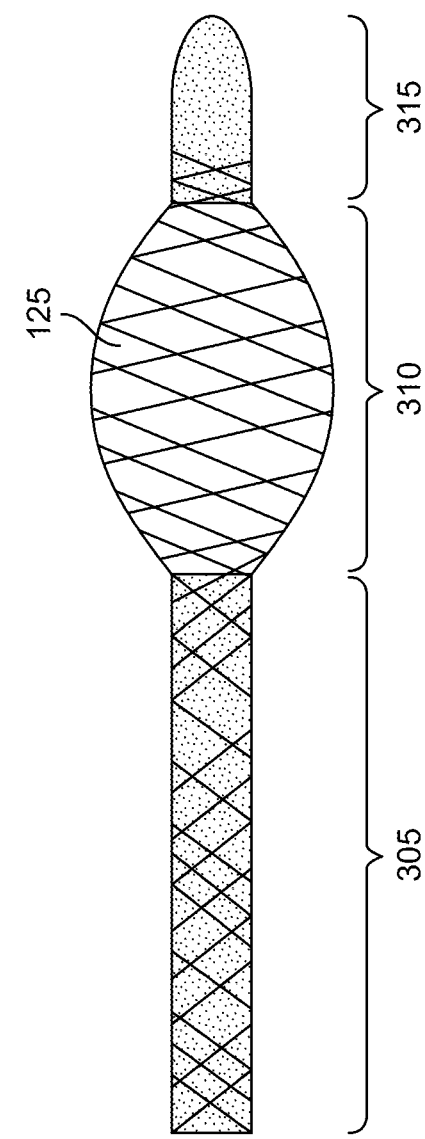
FIG. 6A
FIG. 6B

OCULAR IMPLANT WITH FLUID OUTFLOW PATHWAYS HAVING MICROPOROUS MEMBRANES

REFERENCE TO PRIORITY DOCUMENT

This application claims priority of U.S. Provisional Patent Application Ser. No. 61/353,147, entitled "Ocular Implant with Fluid Outflow Pathways Having Microporous Membranes" by Thomas A. Silvestrini, filed Jun. 9, 2010. Priority of the filing date of Jun. 9, 2010, is hereby claimed, and the disclosure of the provisional patent application is hereby incorporated by reference in its entirety.

BACKGROUND

This disclosure relates generally to methods and devices for use in treating glaucoma. The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Past treatment includes the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humor from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

Current devices and procedures for treating glaucoma have disadvantages and only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap are prone to infection, and can occlude and cease working. Further, wound healing and the postinflammatory processes caused by the local trauma of an implantation procedure can contribute to device failure due to occlusion of fluid outflow ports. This can require re-operation to remove the device and place another one, or can result in further surgeries.

In view of the foregoing, there is a need for improved devices and methods for the treatment of glaucoma.

SUMMARY

Disclosed are devices and methods for treatment of eye disease such as glaucoma. An implant is placed in the eye wherein the implant provides a fluid pathway for the flow or drainage of aqueous humor from the anterior chamber to the suprachoroidal space. The implants described herein are designed to enhance aqueous flow through the normal outflow system of the eye with minimal to no complications. The implants described herein include a microporous film or membrane that prevents cellular infiltration while allowing for fluid flow through the implant. Any of the procedures and devices described herein can be performed in conjunction with other therapeutic procedures, such as laser iridotomy, laser iridoplasty, and goniosynechialysis (a cyclodialysis procedure).

In an embodiment, disclosed herein is an ocular implant having an elongate member having a flow pathway; at least one inflow port communicating with the flow pathway; and a plurality of outflow openings communicating with the flow pathway. The outflow openings are spanned by an elastomeric membrane having a plurality of pores in fluid communication with the flow pathway. The elongate member is adapted to be positioned in the eye such that the inflow port communicates with the anterior chamber and the outflow openings communicate with the suprachoroidal space.

The elongate member can further include a braided structure having a plurality of interwoven struts. The braided structure can be adapted to transition between a first shape when in tension and a second shape upon release of tension. The outflow openings can include gaps between the plurality of interwoven struts. The elastomeric membrane spanning the outflow openings can additionally surround each of the interwoven struts. The elastomeric membrane surrounding each of the interwoven struts can expand and contract upon movement of the interwoven struts. The elastomeric membrane can be a material including polyurethane, silicone, Lycra, and Hytrel. Each of the pores can be sized to achieve aqueous fluid flow through the outflow openings and substantially prevent passage of material into the outflow openings. Each of the pores can have a diameter that is less than 1 micron. Each of the pores can have a diameter between about 0.1 microns to 0.8 microns. The elastomeric membrane can have a pore density between about 1 pore per square micron to 10 pores per square micron. The implant can further include a second membrane coating the elastomeric membrane. The second membrane can include hydrogel. The second membrane can include fibers spanning the pores. The second membrane can span at least a portion of each of the plurality of pores in the elastomeric membrane.

Other features and advantages should be apparent from the following description of various embodiments, which illustrate, by way of example, the principles of the invention.

BRIEF DESCRIPTION OF THE DRAWINGS

FIG. 6A shows an embodiment of an implant at least partially formed of a braided structure.

FIG. 6B shows the implant of FIG. 6A in an expanded state.

DETAILED DESCRIPTION

Figure 1:
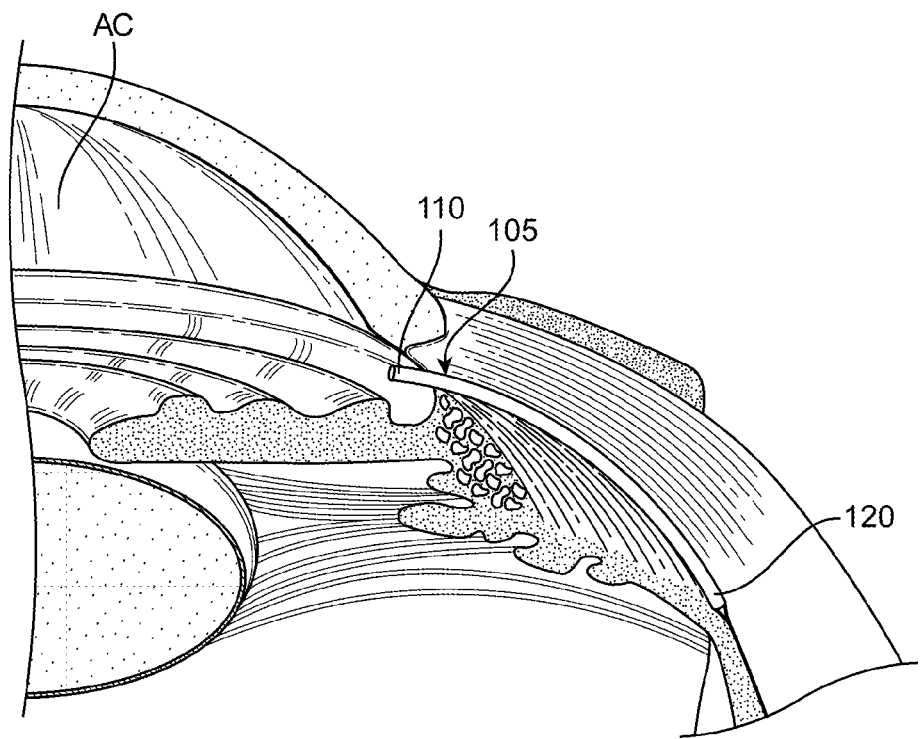
FIG. 1 is a cross-sectional, perspective view of a portion of the eye showing the anterior and posterior chambers of the eye.

FIG. 1 is a cross-sectional, perspective view of a portion of the eye showing the anterior and posterior chambers of the eye. A schematic representation of an implant 105 is positioned inside the eye such that a proximal end 110 is located in the anterior chamber AC and a distal end 120 is located in or near the suprachoroidal space (sometimes referred to as the perichoroidal space). The suprachoroidal space can include the region between the sclera and the choroid. The supraciliary space can also include the region between the sclera and the ciliary body. The implant described herein is not necessarily positioned between the choroid and the sclera. The implant may be positioned at least partially between the ciliary body and the sclera or it may be at least partially positioned between the sclera and the choroid. The implant may also be at least partially positioned in the suprachoroidal space. In any event, the implant provides a fluid pathway between the anterior chamber and the suprachoroidal space.

The implant 105 can be an elongate element having one or more internal lumens through which aqueous humor can flow from the anterior chamber into the suprachoroidal space such as in the region between the sclera and the choroid. Fluid flow through or around the implant 105 can provide a therapeutic effect of reduced intraocular pressure within the anterior chamber. At least a portion of the implant has a structure that includes a plurality of openings covered by a membrane, film or other material that is porous. The openings, for example, can be layered, covered or otherwise spanned by an elastomeric film that has micropores allowing for fluid flow out of the internal lumen while inhibiting cellular infiltration and blockage of the openings. The implants described herein are also adapted to change from a first shape configured for insertion into the eye to an expanded second shape, for example to retain the implant in the eye.

Eye Anatomy

Figure 2:
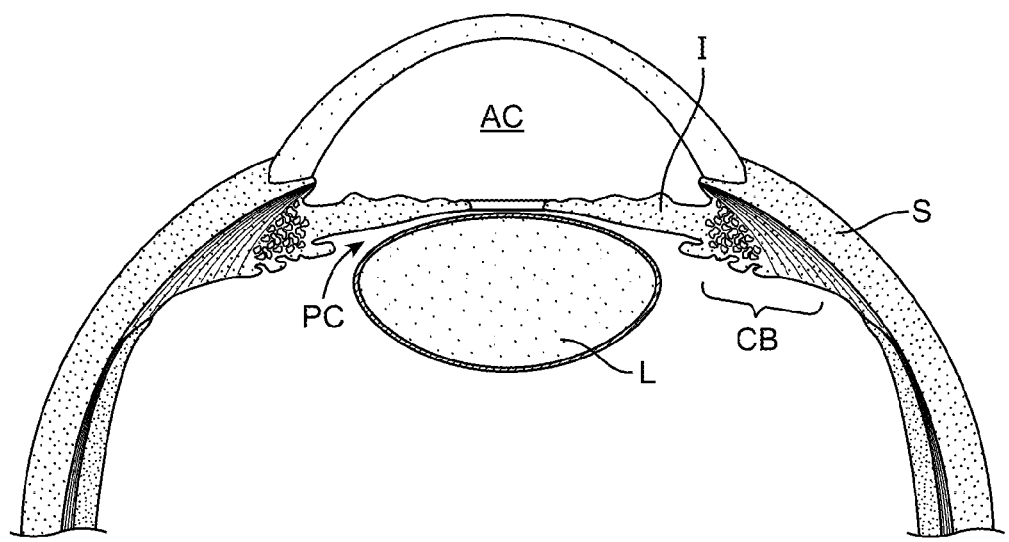
FIG. 2 is a cross-sectional view of a human eye.

FIG. 2 is a cross-sectional view of a human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance.

The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

General Implant Structure

Figure 3A:
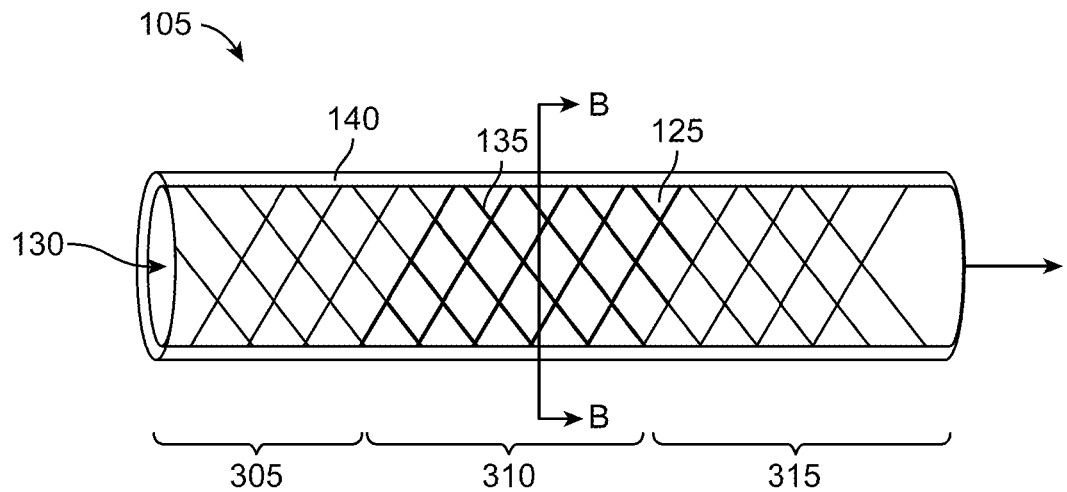
FIG. 3A shows a schematic side view of an embodiment of an implant having a microporous membrane.

FIG. 3A shows an embodiment of an implant 105 having a tubular or partially tubular structure. The implant 105 can include a proximal end, a distal end, and a structure extending between the two that permits fluid (such as aqueous humor) to flow along the length of the implant 105 such as through the implant 105 or around the outside of the implant 105. The implant 105 can include at least one internal lumen 130 having at least one inlet for ingress of fluid (such as aqueous humor from the anterior chamber) and at least one outflow opening for egress of fluid. The implant 105 can include various arrangements of fluid outlets that communicate with the lumen(s) 130, as will be described in more detail below. The implant 105 can also have an open-ended type structure or can have a closed structure. The implant can be a tube-like structure with cut outs such as like a cage that springs open like a cardiovascular stent.

The internal lumen 130 can serve as a passageway for the therapeutic outflow of aqueous humor through the implant 105 directly from the anterior chamber to the suprachoroidal space. In addition, the internal lumen 130 can be used to mount the implant 105 onto a delivery system. The internal lumen 130 can also be used as a pathway for flowing irrigation fluid into the eye generally for flushing or to maintain pressure in the anterior chamber, or using the fluid to hydraulically create a dissection plane into or within the suprachoroidal space.

The implant 105 can have a substantially uniform diameter along its entire length, although the diameter and shape of the implant can vary along its length. Moreover, the implant can have various cross-sectional shapes (such as a circular, oval or rectangular shape) and can vary in cross-sectional shape moving along its length. The cross-sectional shape can be selected to facilitate easy insertion into the eye. The implant 105 can also include retention structure(s) disposed on the outside of the implant (not shown). It should also be appreciated that features described with respect to one embodiment can be used with other embodiments described herein.

As mentioned above, the implant 105 can include various arrangements of fluid outlets that communicate with the lumen(s) 130. These fluid outlets can be coated, spanned or otherwise covered by a material, such as a microporous membrane or other material as will be described in more detail below. The implant 105 can incorporate a structure having one or more openings 125 that fluidly communicate with the internal lumen 130 or other passageways for fluid flow through the implant 105. The spatial configuration, size, quantity, shape and angle of the openings 125 can vary and can be selected to achieve a desired intraocular pressure of the eye as a result of the flow of aqueous humor through the implant. The openings 125 can be formed by gaps between braided struts (see FIG. 3A) or a cage-type structure making up at least a portion of the implant. The openings 125 in fluid communication with an internal lumen 130 can also be located on a side wall interspersed along the length of the implant 105 (see FIG. 7A-7B). The openings 125 facilitate the flow of fluid into and out of the internal lumen of the implant 105.

The openings 125 can be positioned so as to align with predetermined anatomical structures of the eye. For example, one or more openings 125 can align with the suprachoroidal space to permit the flow of aqueous humor into the suprachoroidal space, while another set of openings 125 aligns with structures proximal to the suprachoroidal space, such as structures in the ciliary body or the anterior chamber of the eye.

Figure 4:
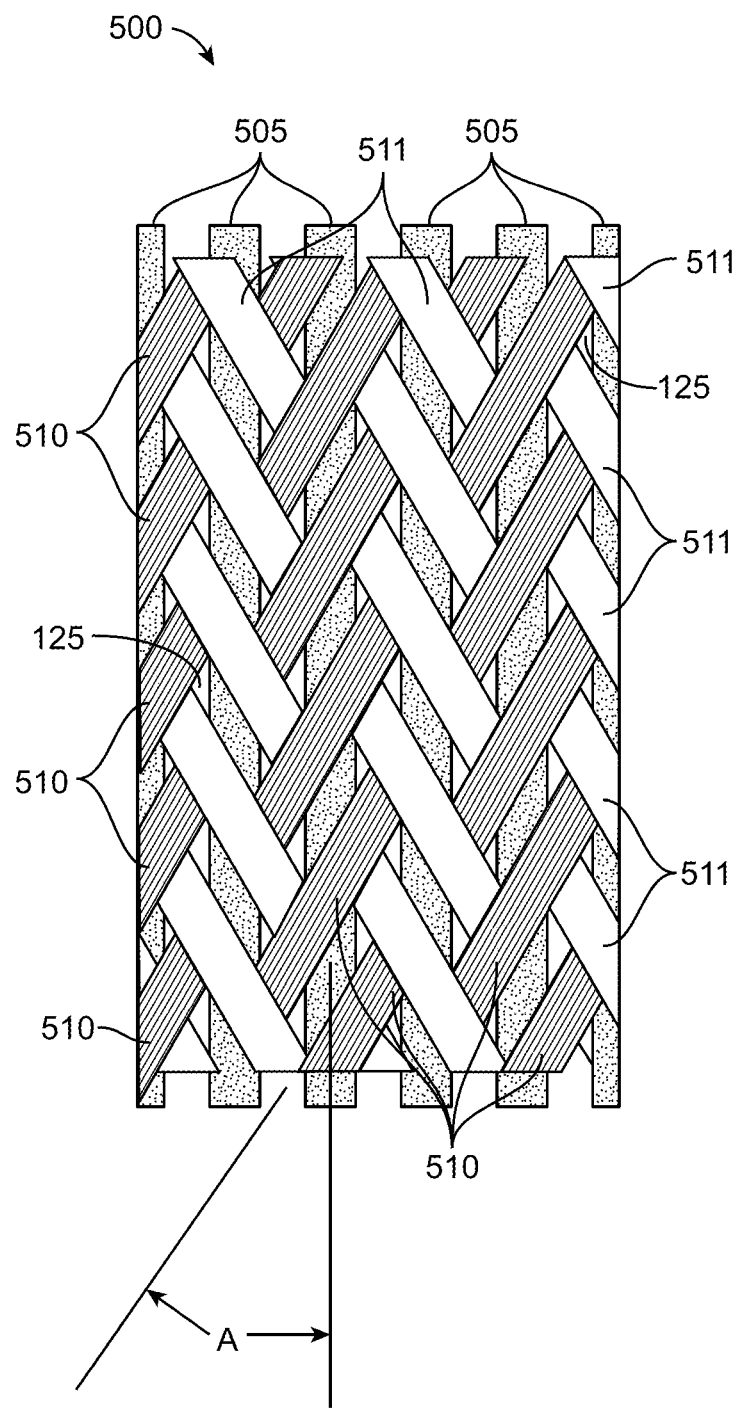
FIG. 4 shows an exemplary embodiment of a section of the braided structure of the implant of FIG. 3A.

In an embodiment, the implant 105 can be at least partially manufactured of a mesh or braided structure formed of two or more interwoven strands, fibers, struts or threads of material. FIG. 4 shows an exemplary embodiment of a section of braided structure 500 of an implant. It should be appreciated that the structure of FIG. 4 is an example and that the braided structure can have other arrangements. The interwoven strands can be arranged in a pattern that forms openings 125 therebetween. The openings 125 can have a diamond, triangular, rectangular or other shape. The braided structure 500 can be positioned over or otherwise combined with a solid tube (not shown) wherein the solid tube has an internal lumen through which fluid can travel. Thus, the braided structure 500 and the solid tube collectively can form a braid-reinforced structure. In the exemplary embodiment shown in FIG. 4, the braided structure 500 is a triaxial braid structure having a plurality of axial members 505 that extend generally parallel to the longitudinal axis of the implant. The braided structure 500 forms a three dimensional tube shape. A plurality of cross-members 510, 511 can be arranged diagonal to the axial members 505 at a braiding angle A relative to the axes of the axial members 505. In cross-section, the axial members 505 and cross-members 510, 511 can collectively form a cylinder or another three-dimension shape having an internal lumen. The axial members 505 can be elastic (e.g., formed of an elastomer) while the cross-members 510, 511 can be formed of a high-strength material. The braids can be arranged in a variety of patterns including, but not limited to, a one-over pattern, diamond pattern, non-diamond pattern. The axial members or cross-members can be flat banded fibers. That is, the members can have flat outer surfaces and can be rectangular in cross-section. The implant can have an open-ended stent type structure. The implant can be a cage-type structure such as a tube with cut-outs. The implant can be a swaged tube that can be cut out in different patterns and heat set. The implant can have gathered ends.

The implant 105 can have any of a variety braided structures and non-braided structures that are connected and arranged in various manners. With reference again to FIG. 3A, the implant 105 can have a proximal section 305, a central section 310, and a distal section 315. The proximal section 305 can be formed of a solid tube (with an internal lumen) that is overlaid with a braided structure such that the proximal section 305 is a braid-reinforced section. Similarly, the distal section 315 can be a solid tube (with or without an internal lumen). The distal section 315 can be overlaid with a braided structure, partially overlaid or not overlaid with a braided structure. The proximal 305 and distal 315 sections can be "closed" in that the solid structure blocks the openings 125 between the strands 135 of the braided structure, where present. The central section 310, in contrast to the proximal 305 and distal 315 sections, can be formed entirely of a braided structure. The central braided section 310 can be "open" in that the openings 125 between the braided strands are not covered by a solid structure that blocks flow and as such fluid flows through the openings 125 in the central section 310 in an unimpeded manner. Generally, braided structures have less stress at the struts such that the stress gets redistributed to the coating spanning or between the struts. The coating can be flexible such that the redistributed stress does not pose a significant problem.

In another embodiment, the implant can include an elongate wick member through which fluid can flow. The wick member can be formed of a single strand of material or can be formed of a plurality of strands that are interconnected, such as in a twisted, braided, or woven fashion, and through or along with fluid can flow. The wick member(s) do not necessarily include internal lumens, as flow through the wick member can occur via capillary action. In the case of a solid polymer wick, certain surface detents can provide flow lumens between the central body member and the tissue of the suprachoroidal space. The wick member can be combined with a braided structure overlaying the wick member and having a membrane spanning the struts of the braids.

The implants described herein can have any of a variety of braided structures and non-braided structures that are connected, arranged and combined in various manners and geometries. For example, the proximal section and distal section can be formed of braided structures and the central section can be formed of a solid structure that is overlaid or partially overlaid with a braided structure. Alternatively, all three sections of the implant 105 can be manufactured entirely of a braided, open-ended structure similar to a stent or a cage. The implant can also be close-ended with a solid tip having no distal outlet port. In such an embodiment, the fluid can flow out openings in the implant as described above. Any of the sections can have an internal lumen that extends through the section. In any of the embodiments, the ends of the braided structure can be gathered and held in place by an adjacent solid structure, such as a bullet nose at the distal tip of the implant or a tube at the proximal tip.

Membranes Covering Implant Openings

Fibroblasts and fibroblast-derived extracellular matrix proteins play an important role in wound healing, but can be problematic when it comes to maintaining patency of a implant delivered to the eye. For example, openings in the implant can become clogged with cellular material that prevents fluid flow through the implant. The openings 125 of the implants described herein can be partially coated, filled, covered or otherwise spanned by a material or mixture of materials that prevent unwanted tissue, cellular or other in-growth into the openings 125 when the device is implanted in the eye.

Figure 3B:
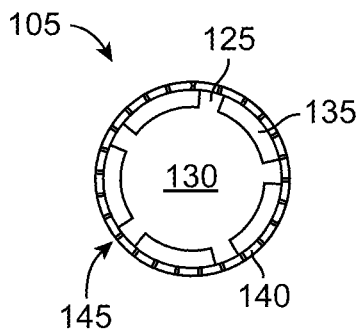
FIG. 3B shows the implant of FIG. 3A in cross-section taken along arrow B-B.
Figure 3C:
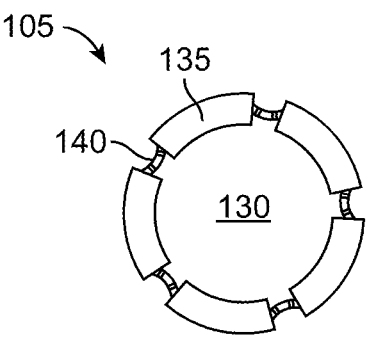
FIGS. 3C-3D show cross-sectional schematic views of other embodiments of implants having a microporous membrane.
Figure 3D:
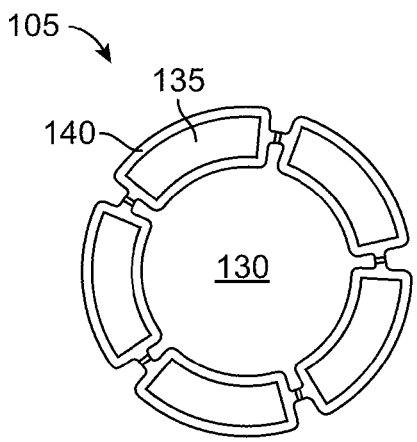

FIGS. 3A-3B show an embodiment of an implant 105 where the braided central portion 310 is covered by a membrane 140. The membrane 140 can cover the openings 125 between the braid struts 135 as well as the struts 135 themselves. Alternatively, the membrane 140 can span between the braid struts 135 (see FIG. 3C) or can completely coat each strut 135 as well as span between the struts 135 (see FIG. 3D).

The membrane 140 can include pores 145 that extend through the membrane 140 such that fluid can flow out of the internal lumen 130 through the pores 145. In an embodiment, the membrane 140 is a microporous membrane and the pores 145 are sized such that they exclude larger particles such as cells from infiltrating the implant, but still allow for fluid flow through the opening 125 out of the internal lumen 130 of the implant 105. Microporous membranes can be used to filter particles generally in the range of 0.1 microns to 10 microns. Fibroblasts, for example, generally have a diameter of about 10-12 microns but are known to migrate through micropores as small as 1 micron. Thus, the membranes 140 described herein have pores 145 generally smaller than 1 micron in diameter and more particularly, within a range of 0.1 microns to 0.8 microns in diameter. Micropores in this size range prevent cellular migration of cells such as fibroblasts and some bacteria as well as the accumulation of other unwanted particles into the implant, but are not so small that they choke off flow through the implant.

A membrane 140 covering or spanning the openings 125 can be flow restricting and cause a bottle neck of aqueous flowing from the anterior chamber. Thus, the surface area the membrane 140, as well as pore density and pore size are each carefully selected based on the structural features and dimensions of the implant to ensure the membrane 140 does not become too restrictive of flow from the anterior chamber. The surface area of the microporous membrane can be increased to optimize flow through the membrane (and the implant) such that the membrane is not the most restrictive element of the implant.

The membranes 140 used to span the openings 125 in the implants described herein can vary. In an embodiment, the membrane can be a stretched microporous membrane, capillary pore microporous membrane, sintered microporous membrane, or a phase inversion microporous membrane. The membranes 140 can be manufactured of a variety of materials and are generally elastomeric. As will be described in more detail below, the implants disclosed herein can have shape change capabilities. As such the membrane 140 also can change shape with the implant 105. Examples of membrane 140 materials considered herein include, but are not limited to, polyurethane, silicone, polycarbonate, polyester, polypropylene, polysulfone, polyethylene, polyethylene terephthalate (PET), Nylon, LYCRA, HYTREL, PVDF and PTFE. Other materials are considered as well, for example, membranes including, but not limited to, extruded and bonded Tyvek fibers (Dupont) can be used to span the openings 125 in the implant 105.

The membranes 140 can also be manufactured by a variety of processes as are known in the art such as pressing and sintering of polymer powder, stretching of extruded polymer sheets, track-etching, or phase inversion. For example, and implant 105 having a braided structure can be dip-coated in a film material, for example of polycarbonate, polyester, or polypropylene that can result in webbing of the material across the openings 125 between the braid struts 135. This film material can then be treated to create pores to be described in more detail below. The implant can be covered or coated with material such that a low profile is maintained, for example using well-known sputtering techniques.

In an embodiment, the membrane 140 can have pores 145 formed using track-etching technology (e.g. Nuclepore or Cyclopore membranes by Whatman). The braided portion of the implant can be covered or dipped in a polymer film, such as polycarbonate or polyester. The film can then be subjected to bombardment by massive energetic nuclei that pass through the film leaving sensitized tracks where the chemical bonds in the polymer backbone are broken. The irradiated film can then be subjected to an etching process that selectively dissolves the narrow trails of radiation-damaged regions leaving cylindrical, uniform pores through the film. The pore size can be controlled by varying the temperature, concentration and residence time in the etch bath as is known in the art. The pore size can be less the 1 micron and is generally in the range of 0.1-0.8 microns. The pore density (pores per unit area) can be controlled by residence time in the irradiator and can be in the range of 1-10 pores/micron$^2$ In another embodiment, the implant can include a microporous phase-inversion membrane covering or spanning the openings 125 of the braided structure. Microporous phase inversion membranes are prepared by dissolving a polymer in an appropriate solvent and spreading it into a liquid film. A precipitant is added to the film from the vapor phase, causing separation of the polymer solution into a solid polymer and a liquid solvent phase. The precipitated polymer forms a porous structure containing a network of pores. Varying the polymer, polymer concentration, precipitation medium and precipitation temperature, the membranes can be made to have a range of pore sizes. Polymer materials can include, but are not limited to, Nylon, polysulfone, PVDF, polypropylene, or polyethylene. The micropores can be interconnecting passages that extend from one surface to the other. The passages provide tortuous tunnels through which fluid can pass out of the implant, but larger particles are filtered out and prevented from entering the implant. The solvent can be removed rapidly such as by heat or use of a coagulating solvent to create voids in the polymer cast. Alternatively, salts can be dissolved in the cast polymer such that water can be used to dissolve the salt leaving voids. These voids become the pores that allow fluid flow through the membrane.

The implants described herein can also include combinations of materials covering the openings 125. For example, a first filter layer having pores can be plugged with or covered be an additional layer of material. The second layer of material can affect one or more properties of the first layer of material. For example, the combination of materials can provide the implant with the appropriate flow characteristics such as by adjusting the pore size of the first membrane. As an example, a membrane having a pore size larger than 0.8 microns can be combined with a second material layer that effectively reduces the pore size to be within a desired range that prevents unwanted materials from entering the implant through the openings. The second material layer can vary and can include any of the membrane materials described herein. The second material also need not be a layer, but can be a semi-porous plug inserted in the pores, for example a polyester plug or sponge-type material.

Figure 5A:
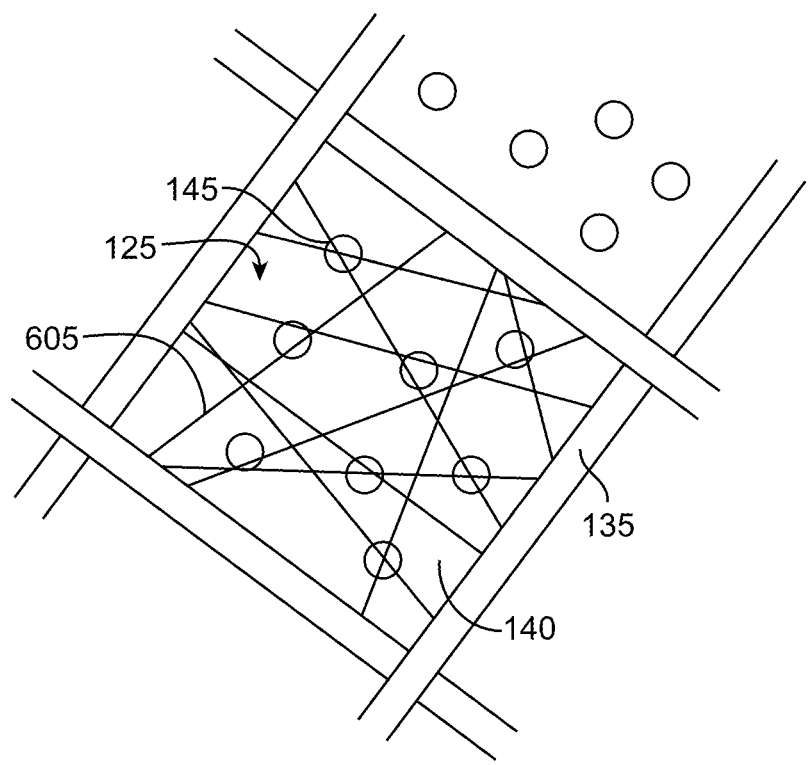
FIGS. 5A-5C show schematic views of section of a braided structure of an implant having a combination of materials.
Figure 5B:
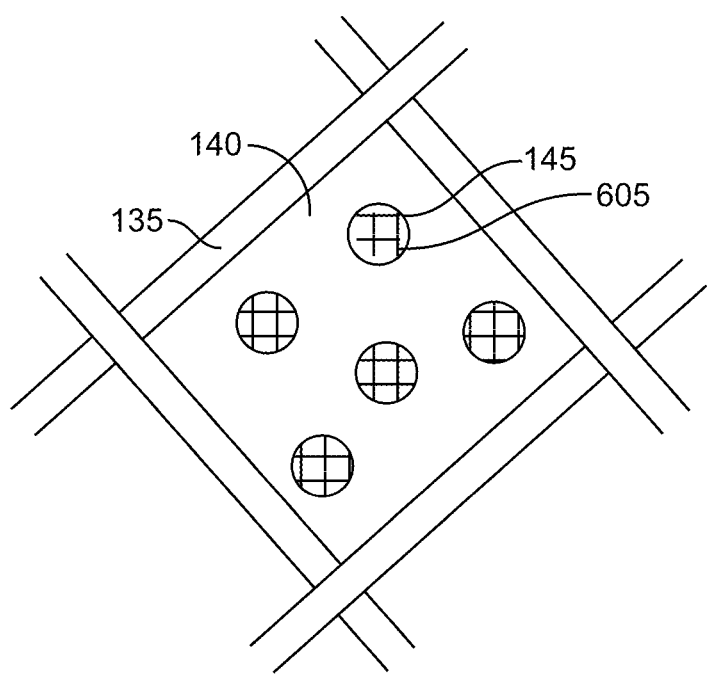

FIGS. 5A-5B show examples a membrane 140 spanning an opening 125 and having a second layer of small fibers 605. The fibers 605 can span the entire opening 125 as shown in FIG. 5A or the fibers 605 can span just the pore 145 present in a membrane 140 as shown in FIG. 5B. The fibers 605 can be a variety of materials, such as the Tyvek fibers described above or electrospun, ultra-fine or nanofibers.

Figure 5C:
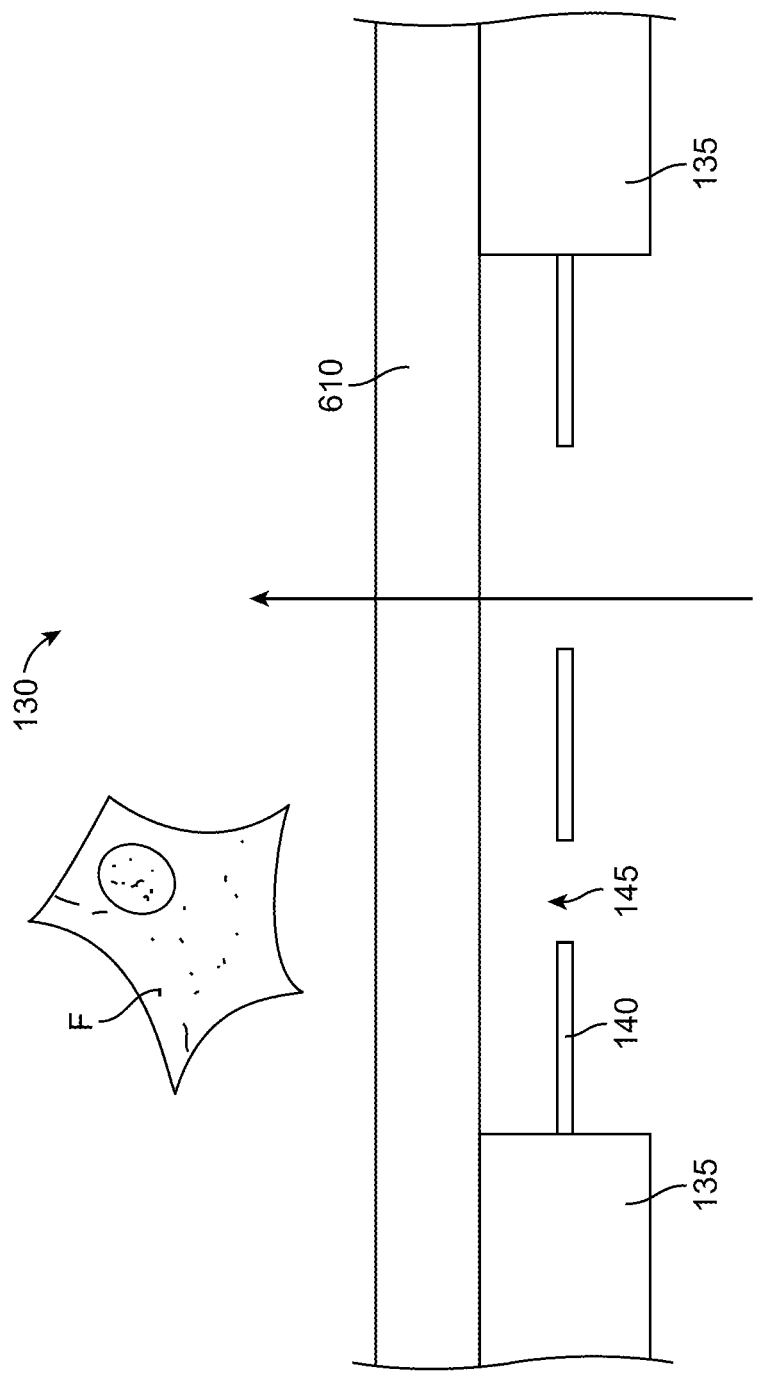

FIG. 5C illustrates another embodiment of an opening 125 spanned by a combination of materials. In this embodiment, struts 135 of the braided structure are spanned by a membrane 140 having micropores 145 as well as a layer of Hydrogel 610 (i.e. a film coating a film coating). In this embodiment, aqueous humour can pass through the pore 145 and the Hydrogel layer 610, but cells and cellular proteins are prevented from entering the opening 125. Incorporating a Hydrogel layer 610 has the added advantages of being slippery and aiding in deployment of the implant into the eye. Hydrogel layer 610 can act as a retention feature due to expansion in the presence of water. Hydrogel is also known to repel fibroblasts F. U.S. Patent Publication Number 2009-0182421 describes ocular implants including Hydrogel layers and is incorporated by reference in its entirety herein.

Any of the embodiments of the implants described herein can be further coated on the inner or outer surface with one or more drugs or other therapeutics materials. The drug or therapeutic agent can be applied in a number of ways as is known in the art. For example, the drug or therapeutic agent can be embedded in the membrane or another polymer (nonabsorbable or bioabsorbable) that is coated on the implant. The therapeutic agents considered herein can vary and include, but are not limited to, a steroid, an antibiotic, an anti-inflammatory agent, an anti-coagulant, an anti-glaucomatous agent, an anti-proliferative, or any combination thereof. The therapeutic agents can maintain the patency of the lumen or openings. The therapeutic agents can also encourage in-growth of tissue in select locations along the length of the implant, for example to assist with retention of the implant within the eye or to prevent leakage around the implant.

It should be appreciated that the description of membranes, materials and manufacturing techniques provided herein are for example and are not intended to be limiting. Other membranes, materials and manufacturing techniques are considered herein. Further, it should also be appreciated that materials, processes and features of the implants and membranes described in the context of separate embodiments can also be implemented in combination in a single embodiment. Conversely, various materials, processes and features of the implants and membranes that are described in the context of a single embodiment can also be implemented in multiple embodiments separately or in any suitable sub-combination.

Shape Change of Implants

As mentioned above, the implants described herein can be configured to transition between a first state of reduced size and a second state of expanded size and vice-versa. The implants can change shape, during or after implantation in the eye. For example, during delivery the implant can be constrained in a reduced radial size or profile or a shape that is substantially uniform and linear. Once the implant is positioned in the eye, the implant can be released to permit shape change that, for example, facilitates anchoring in the eye and prevents migration of the implant once it is positioned in the eye.

The shape change can occur in a variety of manners. For example, the implant can be manufactured of a material such as Nitinol that deforms in response to temperature variations or a release of a constraining element. Thus, the implant can be self-expanding or self-restricting at various locations along the length. In another embodiment or in combination with a self-expanding implant, the implant can be expanded manually, such as through use of an expansion balloon or by passing the implant along a pre-shaped device, such as a reverse-tapered delivery trocar that increases in diameter. In addition, the implant can be positioned inside a sheath during delivery wherein the sheath maintains the implant in the first state of reduced size. Upon delivery, the sheath can be removed to permit the implant to expand in size, such as in a manner described herein.

The change in shape can be an outward expansion or can be any other change in shape, such as to change from a straightened to a non-straightened (e.g., curved or wavy) shape. In an embodiment, the implant can have a structure that is spring-loaded or biased such that strands of the braid can move relative to one another or deform so that the implant springs open. The strands of the braid can be formed of a material, such as a spring metal or superelastic metal that is heat- or cold-treated or pressure-set to a desired spring-open configuration such as an enlarged configuration. The strands can also be formed of a polymer or can be formed of a composite (fiber-reinforced strands). Alternately, the spring-open action can be provided by the polymer coatings of the openings, the fibers, and/or the fiber cross-over locations in the braided structure. In another embodiment, the braided structure can be at least partially formed of a shape-change material that changes shape in response to predetermined conditions, such as a change in temperature.

FIG. 6A shows an embodiment of an implant 105 in an unexpanded state. FIG. 6B shows the implant of FIG. 6A with a braided central section 310 enlarged to an expanded state. As described above, the braided section 310 can include gaps or openings 125 between the braid struts 135 that are spanned by a membrane 140. The membrane 140 spanning between the struts 135 of the braided section 310 can be elastomeric such that the membrane 140 can move along with the struts 135 as they spread or expand.

In an embodiment, the shape of the proximal section 305 and distal section 315 do not undergo expansion and are unchanged. Alternatively, the proximal and distal sections can undergo some expansion or other shape change (e.g., contraction or expansion) but the amount of expansion is less than the expansion of the braided central section 310.

Figure 7A:
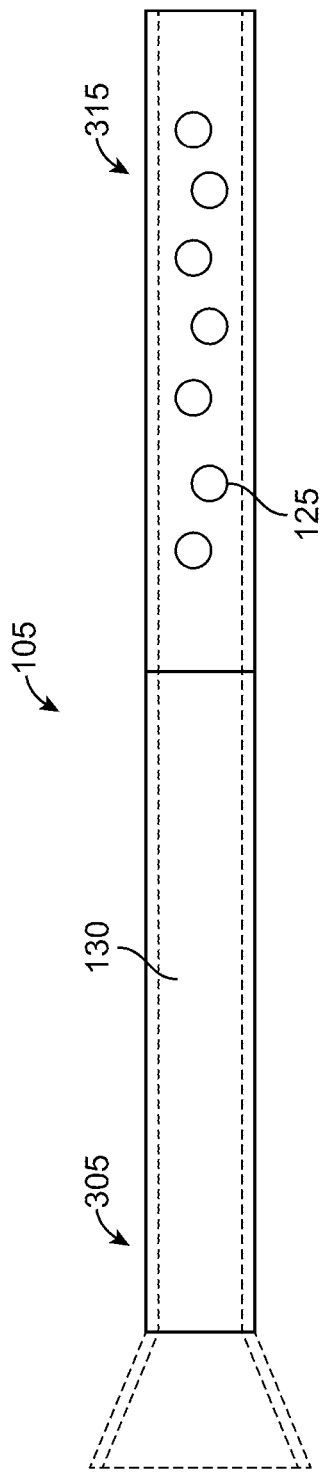
FIG. 7A shows another embodiment of an implant at least partially formed of a shape changing material.
Figure 7B:
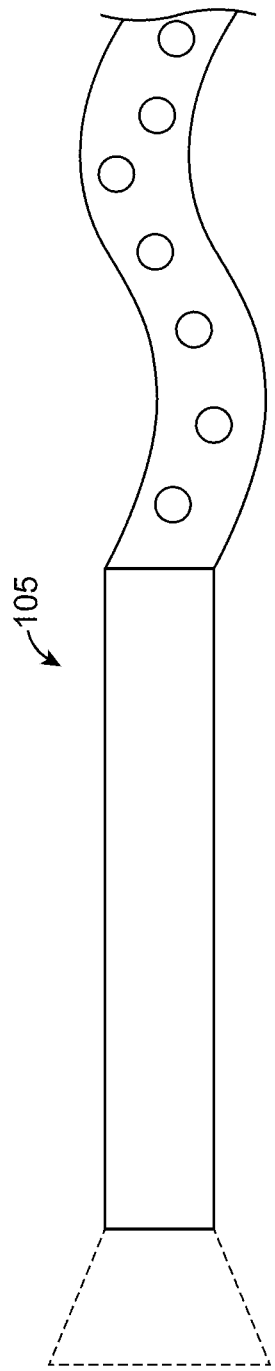
FIG. 7B shows the implant of FIG. 7A in an expanded state.

The shape change implant 105 need not include a braided structure or a stent-like structure (see FIGS. 7A-7B). For example, the implant 105 can be manufactured of a material such as a thermoplastic elastomer (TPE) that is capable of being reversibly deformed between a first, constrained shape to the second, relaxed shape. In an embodiment, the implant 105 can have a distal region 315 that is manufactured of a shape change material. The implant 105 can include various arrangements of openings 125 within the distal region 315 that communicate with an internal lumen(s) 130 of the implant. As with the braided implant variant, the openings 125 of the shape change implant variant can be covered or spanned by an elastomeric, microporous membrane 140.

Additional Implant Features and Materials

The implants described herein can also include additional structural features in addition to the shape change region that assist in anchoring or retaining the implant in the eye. For example, the implant can include one or more retaining or retention features such as a proximal collar, flanges, protrusions, wings, tines, or prongs, that lodge into the surrounding eye anatomy to retain the implant in place and prevent the implant from moving further into the suprachoroidal space. The retention features can also provide regions for fibrous attachment between the implant and the surrounding eye anatomy. The retention feature can also be a coating or layer that expands outward once the implant has been place in the eye. For example, materials such as Hydrogels, foams, lyophilized collagen, or any material that gels, swells or otherwise expands upon contact with body fluids.

The additional retention features can be deformable or stiff and can be made of various biocompatible materials such as described above. For example, the additional retention features can be made from thin 0.001" thick polyimide, which is flexible, thin 0.003" silicone elastomer which is also flexible, or stainless steel or Nitinol. Alternatively, the additional retention features could be rings of polyimide. It should be appreciated that other materials can be used to make the additional retention features and that the shape of additional retention features can vary. Alternatively, the additional retaining features can be manufactured as separate parts and assembled onto the implant as described above. They can fit into grooves, holes or detents in the body of the implant to lock them together. If the additional retaining features are constructed from hairs or sutures, they can be threaded or tied onto the implant. Alternatively, the additional retaining features can be overmolded onto the implant via an injection molding process. In an embodiment, the entire implant and additional retention features can be injection molded in one step. In another embodiment, the additional retaining features can be formed into the implant with a post-processing step such as such as those described in more detail below.

The implants described herein can have one or more features that aid in properly positioning the implant in the eye. For example, the implants can include one or more visual, tomographic, echogenic, or radiopaque markers along the length to assist the user in positioning the desired portion of the implant within the anterior chamber and the desired portion within the suprachoroidal space. In using the markers to properly place the implant, the implant is inserted in the suprachoroidal space, until the marker is aligned with a relevant anatomic structure, for example, visually identifying a marker on the anterior chamber portion of the implant that aligns with the trabecular meshwork, or scleral spur, such that an appropriate length of the implant remains in the anterior chamber. Under ultrasound, an echogenic marker can signal the placement of the device within the suprachoroidal space. Any marker can be placed anywhere on the device to provide sensory feedback to the user on real-time placement, confirmation of placement or during patient follow up. Further, the implants and delivery system can employ alignment marks, tabs, slots or other features that allow the user to know alignment of the implant with respect to the delivery device.

In an embodiment, the implants described herein can have a longitudinal stiffness or column strength sufficient to permit the implant to be inserted into the suprachoroidal space such that the distal tip of the implant tunnels through certain eye tissue (such as the ciliary body) and between certain eye tissues (such as between the sclera and the choroid or between the sclera and the ciliary body) without structural collapse or structural degradation of the implant. In addition, the surface of the inner lumen can be sufficiently smooth relative to a delivery device to permit the implant to slide off of the delivery device during the delivery process. In an embodiment, the column strength can be sufficient to permit the implant to tunnel through certain eye tissues into the suprachoroidal space without any structural support from an additional structure such as a delivery device.

The dimensions of the implants described herein can vary. In an exemplary embodiment, the implant has a length in the range of 0.1" to 0.75" and an inner diameter for a flow path in the range of 0.002" to 0.015". In an embodiment, the inner diameter is 0.012", 0.010", or 0.008". In the event that multiple implants are used, and for example each implant is 0.1", the fully implanted device can create a length of 0.2" to 1.0", although the length can be outside this range. An embodiment of the implant is 0.250" long, 0.012" in inner diameter, and 0.015" in outer diameter. One embodiment of the implant is 0.300" long.

As mentioned, the implants described herein including their shape changing portion(s) can be made of various biocompatible materials. The implant or portion(s) thereof can be made of various materials, including, for example, thermoplastic elastomers, polyimide, Nitinol, platinum, stainless steel, molybdenum, or any other suitable polymer, metal, metal alloy, or ceramic biocompatible material or combinations thereof. The material of manufacture is desirably selected to have material properties suited for the particular function of the implant or portion thereof. In an embodiment, the implants can be manufactured of synthetic polymeric materials that show reversible extension and can be deformed repeatedly such that they return to their "original" shape when the stress is released. The reversible deformation of the implant, even at higher body temperatures, is a desirable characteristic.

The braided implants can be manufactured according to a variety of methods known in the art. The solid portions of the implant can be cast, coated (e.g., dip-coated, vapor-coated, or powder-coated), bonded, trapped (i.e., sandwiched) or otherwise attached into or onto the braided structure. In an embodiment, at least a portion of the implant is reaction cast around reinforcing wire. The strands of the braided portions of the implant can be joined to form a bulb or funnel shape, such as by welding or cold working the strands or by bonding the strands in epoxy or other matrix glues. In addition, the strands can be knotted, encapsulated with a heat shrink, insert injection molded, diffusion bonded, solvent welded, etc. The fiber cross-overs can also be crimp-set during the braiding process. The braided portions of the implants described herein can be braids or wires reinforced with polymer, Nitinol, or stainless steel braid or coiling or can be a co-extruded or laminated tube with one or more materials that provide acceptable flexibility and hoop strength for adequate lumen support and drainage through the lumen.

The shape change portions of the implants described herein can also be formed by one or more post-processing steps as are known in the art. The shape changing portion of the implant can be manufactured by a heating-molding-cooling series of steps to create an implant of a desired retention shape. The implant can be made of a thermally-stimulated, shape-memory polymer, for example thermoplastic PVDF. Polymer pellets can be extruded through a mold to form an elongate, hollow tube. At least a portion of the tubular implant can be exposed again to heat, such as a heated mandrel that heats a portion of the implant, to a temperature above the $T_g$ (glass transition temperature) of the material such that it goes from a rigid, glassy modulus to the rubbery modulus. Once in the rubbery modulus, the implant can be deformed as desired, for example a funnel-shaped collar formed in the proximal portion or an s-shaped curve in the distal portion. The implant can then be cooled below the $T_g$. Upon cooling, the implant will retain this curved shape yet due to the flexible nature of the polymer, stress can be applied to the implant (e.g. inserting a delivery wire through the internal lumen) to temporarily change the shape of the implant to a different shape. As described above, upon removal of the constraint (e.g. removal of the delivery wire), the implant will reversibly deform back into the "retention" shape. The shape changing portion(s) of a thermoplastic implant can be processed by engineering the cross-links such as through heat, flaring, thermo-molding, pressure, chemicals or radiation such as electron beam exposure, gamma-radiation or UV light. Thermosets and cross-linked sets can also be used.

Delivery of Implants

Figure 8A:
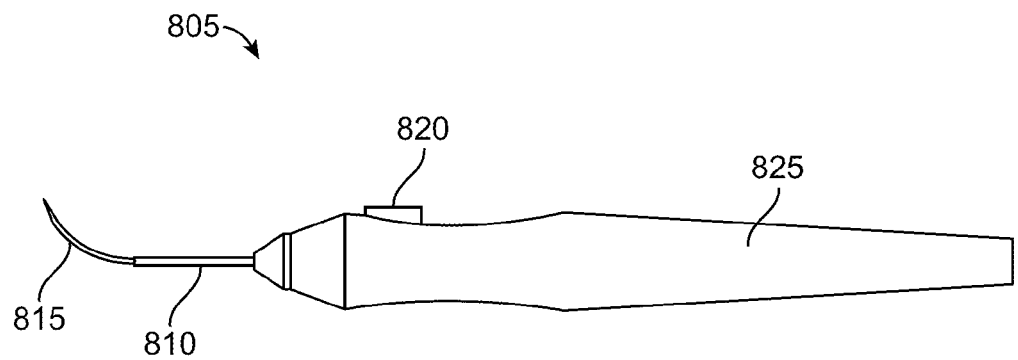
FIGS. 8A-8B illustrate actuation of an implant delivery system.
Figure 8B:
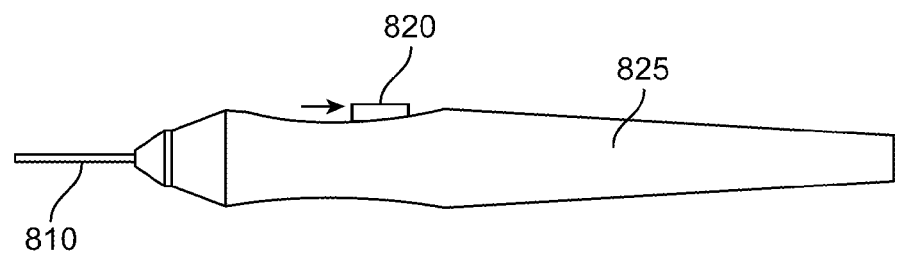

A delivery system can be used to deliver an implant 105 into the eye such that the implant 105 provides fluid communication between the anterior chamber and the suprachoroidal space (see FIG. 8A-8B). The delivery system generally includes a proximal handle component 825 and a distal delivery component. The proximal handle component 825 can include an actuator 820 to control the release of an implant from the delivery component 805 into the target location in the eye. The proximal handle component 825 also can include a channel for insertion of an internal visualization system, such as a fiber optic image bundle. Such a delivery system having an internal visualization system need not be used in conjunction with a gonioscope or viewing lens.

The delivery component 805 includes an elongate applier 815 that inserts longitudinally through the internal lumen of the implant 105 and a sheath 810 positioned axially over the applier 815. Alternatively, the delivery component can include a pusher the presses against the proximal portion of the implant and pushes it out of a delivery sheath. In either embodiment, the sheath 810 can aid in the release of the implant 105 from the delivery component 805 into the target location in the eye. As best shown in FIGS. 8A and 8B, the actuator 820 can be used to control the applier 815 and/or the sheath 810. For example, the sheath 810 can be urged in a distal direction relative to the applier 815 to push the implant 105 off the distal end of the applier 815. Alternately, the sheath 810 can be fixed relative to the handle component 825. In this embodiment, the sheath 810 can act as a stopper that impedes the implant 105 from moving in a proximal direction as the applier 815 is withdrawn proximally from the implant 105 upon actuation of the actuator 820. In a first state shown in FIG. 8A, the applier 815 is extended distally relative to the sheath 810. Movement of the actuator 820, such as in the proximal direction, causes the applier 815 to slide proximally into the sheath 810 as shown in FIG. 8B. This effectively pushes the implant 105 off the distal end of the applier 815 and releases the implant 105 in a controlled fashion such that the target positioning of the implant 105 within the suprachoroidal space is maintained.

An exemplary method of delivering and implanting the implant into the eye is now described. In general, one or more implants 105 can be slidably mounted on and implanted in or near the suprachoroidal space using a delivery system as described herein. The mounting of the implant on the applier of the delivery system can be aided by a retention layer (or a retention coating on the applier or the internal walls of the implant) that reversibly retains the implant on the tip of the applier while still maintaining a flexible and low profile applier. A retention layer can be used to avoid the implant from falling off the applier inadvertently during delivery until the user actuates the delivery component and effects controlled release of the implant from the applier 815, for example, upon proximal withdrawal of the applier 815. The implant 105 is then secured in the eye so that it provides fluid communication between the anterior chamber and the suprachoroidal space.

Each step of implantation can be visualized using an internal visualization system. Visualization can occur continuously during implantation or other procedures without the need for re-positioning or removing one or more components of the imaging systems and without the need for viewing through a goniolens.

The delivery portion 805 is positioned such that the distal tip of the applier 815 and the implant 105 penetrate through a small, corneal incision to access the anterior chamber. In this regard, the single incision can be made in the eye, such as within the limbus of the cornea. In an embodiment, the incision is very close to the limbus, such as either at the level of the limbus or within 2 mm of the limbus in the clear cornea. The applier 815 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane.

The corneal incision has a size that is sufficient to permit passage of the implant on the applier there through. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision.

After insertion through the incision, the applier 815 is advanced into the anterior chamber along a pathway that enables the implant 105 to be delivered from the anterior chamber into the suprachoroidal space. With the applier 815 positioned for approach, the applier 815 can be advanced further into the eye such that the blunt distal tip of the applier 815 and/or the implant 105 penetrates the iris root or a region of the ciliary body or the iris root part of the ciliary body near its tissue border with the scleral spur, to be discussed in more detail below.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. The applier travels along a pathway that is toward the scleral spur such that the applier passes near the scleral spur on the way to the suprachoroidal space, but does not penetrate the scleral spur during delivery. Rather, the applier 815 can abut the scleral spur and move downward to dissect the tissue boundary between the sclera and the ciliary body, the dissection entry point starting just below the scleral spur near the iris root or the iris root portion of the ciliary body.

The applier 815 can approach the iris root from the same side of the anterior chamber as the deployment location such that the applier 815 does not have to be advanced across the iris. Alternately, the applier 815 can approach the location from across the anterior chamber such that the applier 815 is advanced across the iris and/or the anterior chamber toward the opposite iris root. The applier 815 can approach the eye and the iris root along a variety of pathways. The applier 815 does not necessarily cross over the eye and does not intersect the center axis of the eye. In other words, the corneal incision and the location where the implant is implanted at the iris root can be in the same quadrant. Also, the pathway of the implant from the corneal incision to the iris root ought not to pass through the centerline of the eye to avoid interfering with the pupil.

Figure 9:
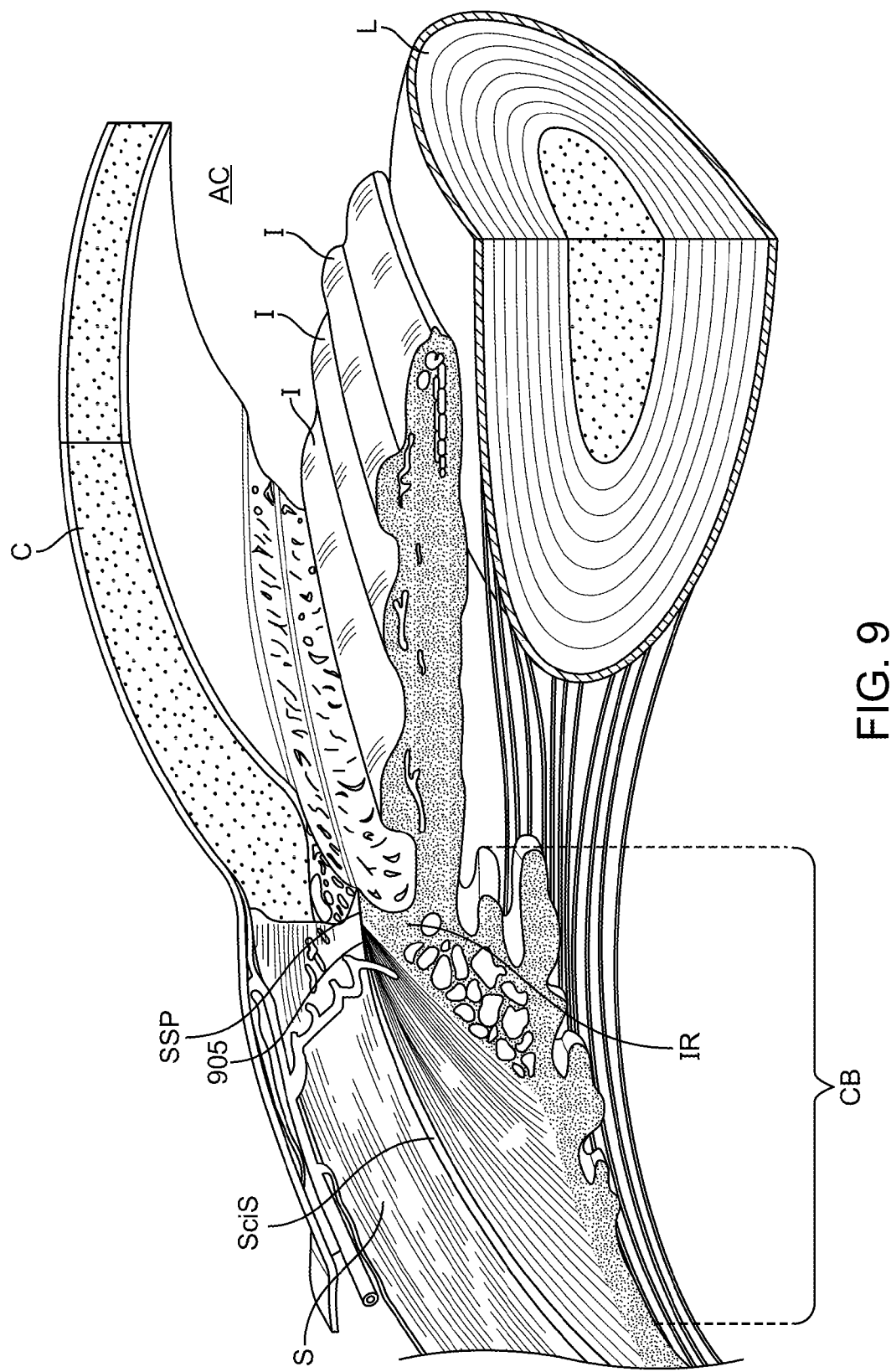
FIG. 9 shows an enlarged, cross-sectional view of the anterior region of the eye.

FIG. 9 shows an enlarged view of the anterior region of the eye showing the anterior chamber AC, the cornea C, the iris I, lens L and the sclera S. The implant 105 mounted on the applier 815 can approach from the anterior chamber AC. As mentioned above, the applier 815 moves along a pathway such that the dissection entry point of the distal tip of the applier 815 can penetrate the iris root IR or the iris root portion of the ciliary body CB near the scleral spur SSp. The surgeon can rotate or reposition the handle of the delivery device in order to obtain a proper approach trajectory for the applier 815, as described in further detail below.

The applier 815 with the implant 105 positioned thereupon is advanced through the iris root IR, the ciliary body CB or the iris root portion of the ciliary body CB. As the applier 815 is advanced it penetrates an area of fibrous attachment 905 between the scleral spur SSp and the ciliary body CB. This area of fibrous attachment 905 can be approximately 1 mm in length. Once the distal tip of the applier 815 penetrates and is urged past this fibrous attachment region 905, it then more easily causes the sclera S to peel away or otherwise separate from the choroid as it follows the inner curve of the sclera and forms the suprachoroidal space SChS. As described above, a combination of the applier's tip shape, material, material properties, diameter, flexibility, compliance, coatings, precurvature etc. make it more inclined to follow an implantation pathway that mirrors the curvature of the inner wall of the sclera and between tissue layers such as the sclera S and choroid.

The applier 815 is continuously advanced into the eye, for example approximately 6 mm. The dissection plane of the applier 815 follows the curve of the inner scleral wall such that the implant 105 mounted on the applier 815 after penetrating the iris root or the iris root portion of the ciliary body, bluntly dissects the boundary between tissue layers of the scleral spur SSp and the ciliary body CB such that a distal region of the implant extends through or into the supraciliary space SCiS. The implant may be positioned between the tissue boundaries of the sclera S and the choroid forming the suprachoroidal space SChS. A first portion of the implant 105 is positioned in communication with the suprachoroidal space SChS and a second portion of the implant 105 remains within the anterior chamber AC. In one embodiment, at least 1 mm to 2 mm of the implant (along the length) remains in the anterior chamber.

Once properly positioned, the implant 105 is released and the shape change portion of the implant allowed to expand. The implant 105 can be released for example by withdrawing the applier 815 such that the implant 105 is effectively pushed in a controlled manner off the tip of the delivery portion 805 with the sheath 810 (for example via the manner described above with reference to FIGS. 8A-8B). A retention layer can optionally be used to assist in retaining the implant 105 on the applier 815 during the steps of delivery. However, the relationship between the retention layer and the implant 105 is readily reversible such that the applier 815 and retention layer can be withdrawn into the sheath 810 to controllably release the implant 105 from the tip of the applier 815 upon arrival at the target location within the eye.

Figure 10:
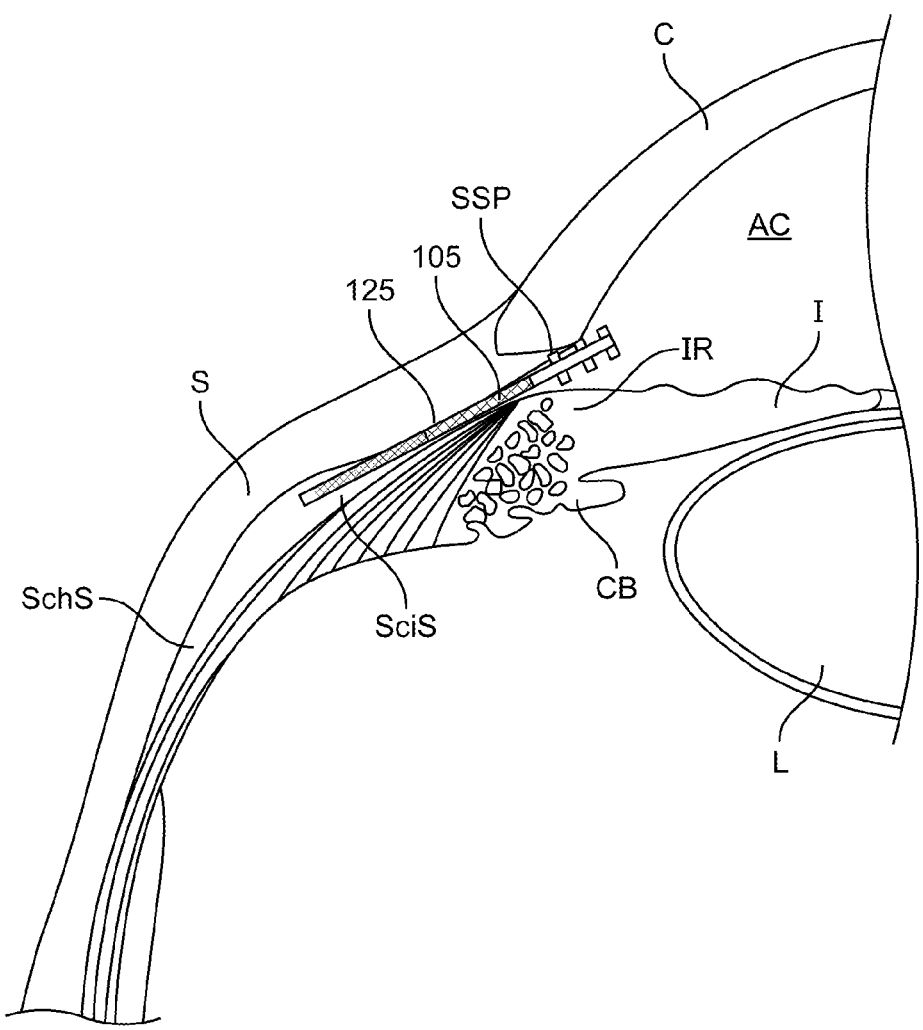
FIG. 10 is a cross-sectional view of a portion of the eye showing an implant within the suprachoroidal space.

The implant 105 is positioned so that a portion of the implant is sitting on top of the ciliary body CB and the shape change portion of the implant expands and openings 125 are positioned for fluid delivery into the suprachoroidal space. The ciliary body CB acts as a platform off of which the implant 105 can cantilever into the suprachoroidal space SChS. The implant 105 has a relative stiffness such that, when implanted, the implant 105 deforms at least a portion of the tissue adjacent the suprachoroidal space to take on a shape that is different than the natural curvature. In this manner, the implant 105 can lift or "tent" the sclera S outward such that the suprachoroidal space SChS is formed around the distal end of the implant 105. The tenting of the sclera S as shown in FIG. 10 has been exaggerated for clarity of illustration. It should be appreciated that the actual contour of the tented region of tissue may differ in the actual anatomy. The implant and the openings can act as a flow pathway between the anterior chamber AC and the suprachoroidal space SChS.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An ocular implant, comprising:
an elongate member comprising:
 a flow pathway;
 at least one inflow port communicating with the flow pathway;
 a plurality of outflow openings communicating with the flow pathway;
 a braided structure having a plurality of interwoven struts and openings formed between the interwoven struts, wherein the braided structure is configured to form a first diameter for insertion through a self-sealing incision in the cornea of an eye and further configured to expand from the first diameter to a second diameter upon implantation in the eye; and
 an elastomeric membrane spanning between at least one of the openings formed by the interwoven struts, wherein the elastomeric membrane is configured to form a first shape when the braided structure forms the first diameter and form a second shape when the braided structure expands to the second diameter,
wherein the elastomeric membrane has a plurality of pores in fluid communication with the flow pathway; and
wherein the elongate member is adapted to be positioned in the eye such that the at least one inflow port communicates with the anterior chamber and the at least one of the openings communicate with the suprachoroidal space.

2. The implant of claim 1, wherein the braided structure is adapted to transition between a first shape when in tension and a second shape upon release of tension.

3. The implant of claim 1, wherein the elastomeric membrane spanning the outflow openings additionally surrounds each of the interwoven struts.

4. The implant of claim 3, wherein the elastomeric membrane surrounding each of the interwoven struts expands and contracts upon movement of the interwoven struts.

5. The implant of claim 1, wherein the elastomeric membrane comprises a material selected from the group comprising polyurethane, silicone, Lycra, and Hytrel.

6. The implant of claim 1, wherein each of the pores are sized to achieve aqueous fluid flow through the outflow openings and substantially prevent passage of material into the outflow openings.

7. The implant of claim 1, wherein each of the pores have a diameter that is less than 1 micron.

8. The implant of claim 7, wherein each of the pores have a diameter between about 0.1 microns to 0.8 microns.

9. The implant of claim 1, wherein the elastomeric membrane has a pore density between about 1 pore per square micron to 10 pores per square micron.

10. The implant of claim 1, further comprising a second membrane coating the elastomeric membrane.

11. The implant of claim 10, wherein the second membrane comprises Hydrogel.

12. The implant of claim 10, wherein the second membrane comprises fibers spanning the pores.

13. The implant of claim 10, wherein the second membrane spans at least a portion of each of the plurality of pores in the elastomeric membrane.

\* \* \* \* \*